United States Patent [19]

Sherwin et al.

[11] Patent Number: 5,288,907
[45] Date of Patent: Feb. 22, 1994

[54] HYDROGENATION OF NITROALKANES TO HYDROXYLAMINES

[75] Inventors: Martin B. Sherwin, Potomac; Puvin Pichaichanarong, Baltimore, both of Md.

[73] Assignee: W. R. Grace & Co.-Conn., New York, N.Y.

[21] Appl. No.: 784,850

[22] Filed: Oct. 30, 1991

Related U.S. Application Data

[63] Continuation of Ser. No. 133,120, Dec. 14, 1987, abandoned.

[51] Int. Cl.$^5$ .......................................... C07C 239/08
[52] U.S. Cl. .................................. 564/301; 564/300
[58] Field of Search ........................... 564/300, 301

[56] References Cited

U.S. PATENT DOCUMENTS

| | | | |
|---|---|---|---|
| 3,173,953 | 3/1965 | McWhorter | 260/583 |
| 3,333,001 | 7/1967 | Albert et al. | 260/583 |
| 3,393,237 | 7/1968 | Forman et al. | 564/300 |
| 4,067,690 | 1/1978 | Cuisia et al. | 21/2.7 R |
| 4,350,606 | 9/1982 | Cuisia et al. | 252/392 |
| 4,602,108 | 7/1986 | McKinnie | 564/2 |
| 4,608,390 | 8/1986 | Summers, Jr. | 514/575 |
| 4,719,224 | 1/1988 | Clemence et al. | 514/443 |
| 4,723,030 | 2/1988 | Davis | 564/300 X |
| 5,166,435 | 11/1992 | Sharma et al. | 564/300 |

OTHER PUBLICATIONS

Koperska et al, Nitroalkane Hydrogenation to N-Hydroxylamines, Przemysl Chemiczny, 49 (10):594 (1970).
Johnson et al. J. Chem. Soc. (1956) pp. 1093-1103 Aliphatic Hydroxylamines—Autoxidation.

*Primary Examiner*—Richard L. Raymond
*Attorney, Agent, or Firm*—Howard J. Troffkin

[57] ABSTRACT

Catalytic hydrogenation of nitroalkane to N-alkylhydroxylamine free base in the absence of transition metal ions, and omission of acid and the resultant free base is storage stable, permitting shipment and storage of 15% aqueous solution for use as oxygen scavenger in boiler feed water treatment.

20 Claims, No Drawings

HYDROGENATION OF NITROALKANES TO HYDROXYLAMINES

This is a continuation of application Ser. No. 133,120, filed Dec. 14, 1987, now abandoned.

BACKGROUND OF THE INVENTION

This invention relates to the preparation of N-alkyl hydroxylamines by the catalytic hydrogenation of a nitroalkane.

Hydroxylamine and its N-alkyl derivatives are valuable oxygen scavengers in boiler feed waters (see, for example, U.S. Pat. Nos. 4,067,690 and 4,350,606) with the N-alkyl hydroxylamines being particularly useful. They are conventionally added to the boiler waters as an aqueous solution of the free base, or, optionally (but less preferably) as the salt. The free base form is regarded as greatly preferred for this use as salt residues are undesirable in the boiler. The salts must be converted to the free base before use, thus adding another process step either at the processing site or at the application site.

Various methods for synthesizing alkyl hydroxylamines are known. Catalytic hydrogenation of a nitroalkane to the corresponding N-alkylhydroxylamine has received considerable attention. This process, as presently conducted, has several serious disadvantages, including: (1) the yield is relatively low; (2) substantial amounts of alkylamine are formed; (3) the free base, when finally recovered, is unstable (that is, not stable under ordinary storage conditions which such material must undergo); and (4) the catalyst rapidly loses its activity and selectivity.

A method of stabilizing the desired N-alkyl hydroxylamines was described in U.S. Pat. No. 3,173,953, to J. R. McWhorter. McWhorter requires the hydrogenation of nitromethane to be conducted with Pd/C in the presence of sulfuric acid to form N-methylhydroxylamine sulfate salt. The sulfuric acid reacts with the N-methylhydroxylamine as it is formed to form the corresponding salt and thereby takes it out of the reaction and prevents overreduction to methylamine. A chelant may be present to remove impurities contributed by the water and the apparatus. The reference shows, by example, the ability to attain high yields of N-methylhydroxylamine sulfate salt (Example 1) but additional steps, including neutralization with a base, are of course necessary if free N-methylhydroxylamine base is to be recovered. These additional steps reduce the overall yield of the free base and may introduce stability-jeopardizing impurities.

Koperska et al., in Przemysl Chemiczny, 49(10), 594-598 (1970), report that hydrogenation of nitromethane over Pd/BaSO$_4$ yields methylhydroxylamine. Although the synthesis was performed both with and without the use of acid, there was no provision made to eliminate the presence of transition metal ions during the formation of the hydroxylamine. In addition, the authors stated that the Pd/BaSO$_4$ catalyst could not be re-used. They also disclosed the use of various other hydrogenation catalyst systems with varying results. For example, Pb/C gave low yield but could be re-used if fresh make-up catalyst was added. One of their poorest performing catalysts was Pd/Al$_2$O$_3$ which gave a yield of methylhydroxylamine of about 15% after 7 hours. Yield of byproduct amine in all cases was at least about 10%.

Johnson et al., J. Chem. Soc., pp. 1093-1103 (1956) indicated that the presence of metal catalyst positively influences the oxygen uptake of hydroxylamines.

The instability of aqueous solutions of N,N-dialkylhydroxylamines also been long recognized. U.S. Pat. No. 3,333,001 (1967) proposed to protect such aqueous solutions against storage instability by the addition of a small amount of a benzothiazole, e.g., mercaptobenzothiazole.

SUMMARY OF THE INVENTION

A nitroalkane is treated with hydrogen under pressure in the presence of a hydrogenation catalyst, in a solvent for the reactants in the absence of an acid and of transition metal. Our invention includes the elimination of an acid (e.g., sulfuric), thought necessary in prior art reductions to fix the alkylhydroxylamine product and withdraw it from the reaction. It was not to be expected that we could omit the acid component of the prior art and thereby improve both the process and the product.

DETAILED DESCRIPTION

Utility of N-alkylhydroxylamine as an article of commerce depends to a considerable extent on its stability. For example, in boiler feed water applications, it is normally made up as a dilute aqueous solution, then shipped, and finally stored on-site for extended periods of time (weeks or even months) before use. It must not decompose or deteriorate during this time.

As an indication of the magnitude of the problem, a 55-gallon steel drum of 15% aqueous solution of free N-isopropylhydroxylamine (NIPHA) formed according to current technology begins deterioration immediately on sealing, and within 30 days will analyze zero product. NIPHA free base formed from its commercially salt (NIPHA.HCl 97% purity) also exhibited instability so that it can not be considered a storage stable material. The conversion of the salt to the free hydroxyl amine was carried out entirely in a metal-free environment and the resultant NIPHA crystals were made into an aqueous solution and stored at 25° C. under nitrogen. After only four days, an assay of the solution showed that only 30% of the original amount of NIPHA remained. One can conclude from this that, when an acid is used in the process to prepare NIPHA sat, as in the prior art, the NIPHA free amine prepared from this salt would not be expected to be storage stable.

In the course of describing the present invention herein, certain terms used have the following meanings:

"Anaerobic" means conditions that exclude air or oxygen. Examples: atmospheres of nitrogen, argon, or other non-oxidizing gases. The concept includes filling a container completely with aqueous solution, thereby avoiding sepernatant vapor altogether.

"Storage-stable" refers to N-alkylhydroxylamine that shows no deterioration on storage for at least three months.

"Plastic" (with reference to containers for solutions of N-alkylhydroxylamine) refers to water-inert materials such as polyolefins (polyethylene, polypropylene); acrylics; polyvinylchloride; polycarbonates; polyurethanes; polyamides; polyimides; polyesters; natural and synthetic rubbers; polyvinyl acetate; and sundry others well-known to those skilled in the art.

"Pd/carrier" means palladium on a carrier, typically 5% Pd on alumina, or 5% Pd on carbon.

"Alkyl or alkane", as used with reference to the reactants and products of the invention, means linear or branched alkyls of 1-18 carbons, preferably 1-3 carbons.

"EDTA" means ethylenediaminetetraacetic acid, and includes the alkali metal salts. The sodium salt may be referred to as EDTANa$_4$.

"HEDTA" means hydroxyethylenediaminetriacetic acid.

"NTA" means nitrilotriacetic acid.

"2-NP" means 2-nitropropane.

"NIPHA" means N-isopropylhydroxylamine.

"DEHA" means N,N-diethylhydroxylamine.

"Parts" and "percents" are by weight unless otherwise stated.

"Transition metals" refers to "Transition Elements" as defined in the IUPAC Periodic Chart of the Elements, viz., elements with atomic numbers 21-32, 39-51, 57-84, and 89-106.

The present invention is directed to a process for forming an N-alkyl hydroxylamine (alkyl=$C_1$-$C_{18}$ hydrocarbon), as the free amine and to the storage stable product.

The process requires the hydrogenation of nitroalkanes ($RNO_2$ where R=$C_1$-$C_{18}$ hydrocarbon) to form the corresponding N-alkyl hydroxylamine. The nitroalkane in an inert solvent is contacted with hydrogen in the presence of a hydrogenation catalyst while being maintained in the absence of an inorganic acid and the absence of transition metal ions, and, particularly, iron and nickel and chromium.

It has been found that N-alkyl hydroxylamines can be formed in high yields and provide storage stable salt free product by maintaining the conditions stated herein that is, to form the desired free hydroxylamine by hydrogenation of a nitroalkane in the absence of an inorganic acid and in the substantial absence of free transition metal ions. The latter can be readily accomplished by performing the hydrogenation and subsequent process steps in non-metallic equipment, such as in glass or glass-lined vessels (i.e. glass-lined autoclave) and the like. Alternately or in combination with the use of non-metallic equipment, the reaction solution can contain (must contain when a metal equipment is used) a sequestering agent in sufficient amount to sequester substantially all of the transition metal ions present during formation of the hydroxylamine product. Thus it was found that high yields of N-alkyl hydroxylamine can be achieved whether or not the hydrogenation was carried out in a standard metal or glass lined autoclave, or the like, by following the presently required conditions.

The process conditions found suitable to form the desired product in high yields are:

Sequestering Agents: The subject process should be (must be when metal reactor used) carried out in the presence of a sequestering agent. Suitable ones include EDTA, tetrasodium N,N'-ethylene-bis (2-(2-hydroxy-4-methyl-phenyl)-glycine) and N,N'-di(2-hydroxybenzyl-trimethylenediamine-N,N-diacetic acid, diethylene triamine pentaacetic acid, hydroxyethylenediamine triacetic acid (HEDTA), nitrilotriacetic acid (NTA), and ethylene bis-N,N'-(2-aminomethyl) pyridine-N,N'-diacetic acid. The most preferred sequestering agent is EDTA or its salts. It has been found that certain known sequestering agents, such as citric acid are ineffective in the subject invention.

Hydrogenation Catalyst: Known hydrogenation catalysts can be used herein. Preferred catalysts are Pd, Pt, Raney Ni and Raney Co. The amount of catalyst may be about 0.1-5 weight %, preferably 1-2% (based on Pd or other metal content) of the nitroalkane. When Pd is used, it can be added as oxide and reduced to metal in the autoclave during the synthesis.

Reaction Solvent: The solvent can be any liquid in which the nitroalkane reactant, and preferably also the n-alkyl hydroxylamine product, is soluble and the solvent is inert to hydrogenation. The preferred solvents are $C_1$-$C_3$ alkanols and water as, for example, methanol, ethanol, propanol, and water. A working range is about 1-2 parts by weight of solvent per part of nitroalkane. We prefer about 1:1.

Hydrogen pressure can vary within the range of about 15-500 psia, preferably about 30-115 psia.

The reaction temperature may be maintained in the range of about 25°-100° C., preferably about 50°-75° C.

The level of EDTA or other chelant can vary in the range of about 0.01-0.1%, preferably about 0.01-0.05% by weight of the nitroalkane, provided however that the amount should not be so much that it causes the reaction pH to rise to 10.

Reaction time is not critical; it can be about 1-14 hours, suitably about 4-6 hours.

The N-alkylhydroxylamine product is recovered by venting the pressure vessel, filtering the catalyst, and crystallizing the N-alkylhydroxylamine free base from methanol or other reaction solvent. The product can be made up immediately into a 10-15 weight % aqueous solution and the solution stored in glass or plastic containers under nitrogen or equivalent anaerobic conditions. As such, the aqueous solution can be factory-stored, shipped, and then customer-stored for at least 3 months. The solution can be used directly in oxygen scavenging in boiler water treatment in known ways, such as described in U.S. Pat. Nos. 4,067,690 and 4,350,606.

The resultant N-alkyl hydroxylamine free base has unexpectedly been found to remain storage stable provided it contains less than 20 ppm of transition metal ions therein. This is true even though the material is substantially free or completely free of sequestering agent. In the former case, the majority of sequestering agent is removed in the purification of the N-alkylhydroxylamine. The later instance is achieved when the formation is carried out in non-metallic equipment.

The following examples are given for illustrative purposes only and are not meant to be a limitation on the subject invention. All parts are by weight except as otherwise indicated.

EXAMPLE 1

Hydrogenation of 2-Nitropropane to N-isopropylhydroxylamine

One to two parts by weight of 5% Pd/Al$_2$O$_3$ was added to 500 parts 2-nitropropane (2-NP) in 500 parts methanol. To this mixture was added 0.25 part ethylenediaminetetraacetate, sodium salt (EDTANa$_4$) (i.e., 0.05% based on 2-NP). The reactor was pressurized to 30-100 psig (45-115 psia) H$_2$ and heated to 50°-75° C. for 4-6 hours with good agitation. Selectivity of 2-NP to N-isopropylhydroxylamine (NIPHA) was 95-98%. 2-NP conversion was 95-99%. After the catalyst was re-used in a second and third run under the same conditions and gave NIPHA selectivity of greater than 95% and 2-NP conversion of over 95% under 6 hours of reaction time.

TABLE I shows the improvement in yield and selectivity when hydrogenating 2-NP in the presence of EDTA.

TABLE I

Hydrogenation of 2-Nitropropane (2-NP) With and Without EDTA

| | Conversion of 2-NP, % | NIPHA[1] % Yield | IPA[2] % Yield |
|---|---|---|---|
| Example 2 - 500 ppm EDTA[3] | 96 | 98 | 1.6 |
| Example 3 (control - no EDTA[3]) | 69 | 65 | 5.8 |
| Example 4 - 500 ppm EDTA[4] | 97 | 96 | 3.4 |
| Example 5 (control - no EDTA[5]) | 88 | 38 | 29 |
| Example 6 (glass reactor[6] - no EDTA) | 99 | 89 | 11 |
| Example 7 (glass reactor[6] EDTA) | 97 | 98 | 2 |

[1] N-isoproylhydroxyamine
[2] Isopropylamine
[3] 300 ml Parr Stainless Steel Autoclave, for 2 hours, 5% Pd/Al$_2$O$_3$
[4] 2-L, Stainless Steel for 2 hours, 5% Pd/Al$_2$O$_3$
[5] Same as (4), for 4 hours
[6] 300 ml Glass-lined Parr Autoclave, 2 hours

EXAMPLE 7

The products of each of the above Examples 1-6 were taken up in water to form a 15% solution of NIPHA. Each solution was placed in a glass container, flushed with N$_2$ gas and sealed to be under anearobic conditions. The material was stored at 60° C. for 90 days. Each sample was analyzed for NIPHA. Samples of Examples 1, 2, 4 and 6 each showed greater than 90% retention of NIPHA. Examples 3 and 5 showed substantially no NIPHA remained.

We claim:

1. A process for forming a storage stable N-alkylhydroxylamine free base comprising hydrogenating nitroalkane under a hydrogen pressure and in the presence of a catalytic amount of a palladium hydrogenation catalyst and of an agent selected from the group consisting essentially of EDTA, tetrasodium N,N'-ethylene-bis (2-(2-hydroxy-4-methyl-phenyl)-glycine) diethylenetriaminepentaacetic acid, ethylene bis-N,N'-(2-aminomethyl) pyridine-N,N'-diacetic acid, HEDTA, NTA, and N,N'-di-(2-hydroxybenzyl) trimethylenediamine-N,N'diacetic acid, said nitroalkane contained in an inert solvent to form a nitroalkane solution which is substantially absent of inorganic acid and of transition metal ions and having a pH of lower than 10 to thereby form storage stable N-alkylhydroxylamine free base and separating the catalyst from the free base, product.

2. The process according to claim 1 wherein the nitroalkane is a C$_1$-C$_3$ nitroalkane.

3. The process according to claim 1 wherein the nitroalkane is 2-nitropropane and the resulting N-alkylhydroxylamine is N-isopropylhydroxylamine.

4. The process according to claim 1 wherein the hydrogen pressure is from about 30 to about 115 psia; the agent is EDTA in about 0.01-0.05 weight percent based on the weight of nitroalkane; the catalyst is present in from about 1 to about 2 weight percent based on the weight of nitroalkane; the solvent is a member selected from the group consisting of methanol, ethanol, propanol, water or mixtures thereof; the reaction temperature is about 50°-75° C.; the reaction time is from about 4 to about 6 hours; and the N-alkylhydroxylamine free base is formed in at least 95 percent yield with not more than 5 percent yield of alkylamine, based on starting nitroalkane.

5. The process according to claim 1 wherein about 500 parts of 2-nitropropane (2-NP), about 500 parts methanol, about 0.05 to 0.25 part EDTA, and about 1 to 2 parts Pd/Al$_2$O$_3$ are heated under about 30 to 115 psia of hydrogen to form storage-stable N-isopropylhydroxylamine (NIPHA) with a selectivity of 2-NP to NIPHA of at least 95% and a 2-NP conversion of at least 95%.

6. The process according to claim 1 wherein the catalyst is recovered and reused in the subsequent process of claim 1.

7. The process according to claim 2 wherein the catalyst is recovered and reused in the subsequent process of claim 2.

8. The process according to claim 3 wherein the catalyst is recovered and reused in the subsequent process of claim 3.

9. The process according to claim 4 wherein the catalyst is recovered and reused in the subsequent process of claim 4.

10. The process according to claim 5 wherein the catalyst is recovered and reused in the subsequent process of claim 5.

11. The process according to claim 1 wherein the palladium hydrogenation catalyst is palladium on a carrier support selected from carbon, alumina or mixtures thereof.

12. The process according to claim 2 wherein the palladium hydrogenation catalyst is palladium on a carrier support selected from carbon, alumina or mixtures thereof.

13. The process according to claim 3 wherein the palladium hydrogenation catalyst is palladium on a carrier support selected from carbon, alumina or mixtures thereof.

14. The process according to claim 4 wherein the palladium hydrogenation catalyst is palladium on a carrier support selected from carbon, alumina or mixtures thereof.

15. The process according to claim 5 wherein the palladium hydrogenation catalyst is palladium on a carrier support selected from carbon, alumina or mixtures thereof.

16. The process according to claim 6 wherein the palladium hydrogenation catalyst is palladium on a carrier support selected from carbon, alumina or mixtures thereof.

17. The process according to claim 7 wherein the palladium hydrogenation catalyst is palladium on a carrier support selected from carbon, alumina or mixtures thereof.

18. The process according to claim 8 wherein the palladium hydrogenation catalyst is palladium on a carrier support selected from carbon, alumina or mixtures thereof.

19. The process according to claim 9 wherein the palladium hydrogenation catalyst is palladium on a carrier support selected from carbon, alumina or mixtures thereof.

20. The process according to claim 10 wherein the palladium hydrogenation catalyst is palladium on a carrier support selected from carbon, alumina or mixtures thereof.

* * * * *